United States Patent [19]
Kim et al.

[11] 4,272,504
[45] Jun. 9, 1981

[54] ANTIBODY ADSORBED SUPPORT METHOD FOR CARCINOEMBRYONIC ANTIGEN ASSAY

[75] Inventors: Yung D. Kim, Lindenhurst; Joseph T. Tomita; Jay R. Schenck, both of Waukegan, all of Ill.

[73] Assignee: Abbott Laboratories, North Chicago, Ill.

[21] Appl. No.: 969,592

[22] Filed: Dec. 14, 1978

[51] Int. Cl.³ .................... G01N 33/48; A61K 43/00; G01T 1/00
[52] U.S. Cl. .................................... 424/1; 23/230 B; 424/12
[58] Field of Search ................. 424/1, 12; 260/112 R, 260/112 B; 23/230 B

[56] References Cited
PUBLICATIONS

Searle et al., J. Immunological Methods, vol. 4, 1974, pp. 113–125.
McPherson et al., Int. J. Cancer:12:42–54, (1973).

Primary Examiner—Benjamin R. Padgett
Assistant Examiner—Christine M. Nucker
Attorney, Agent, or Firm—John J. McDonnell

[57] ABSTRACT

This invention relates to an immunoassay for carcinoembryonic antigen in plasma or sera. Heat-treating the plasma or serum provides a supernatant which is incubated with a solid support having carcinoembryonic antigen antibody adsorbed thereto. Subsequently, the solid support is incubated with a labeled carcinoembryonic antigen antibody. The labeled antibody on the solid support is measured and compared to standards.

7 Claims, No Drawings

ANTIBODY ADSORBED SUPPORT METHOD FOR CARCINOEMBRYONIC ANTIGEN ASSAY

BACKGROUND OF THE INVENTION

This invention relates to assaying the level of carcinoembryonic antigen (CEA) in specimens such as sera or plasma. CEA is recognized as a cancer related antigen and its measurement has been used as a marker in diagnosing cancer.

Methods for measuring the level of CEA in sera or plasma have been described in the prior art [Thomson, et al., Proc. Natl. Acad. Sci. (U.S.) 64 (1969) 161; Hansen, et al., Clin. Res. 19 (1971) 143 and Lo Gerfo, et al., New England J. Med. 285 (1971) 138]. Generally, three different immunoassay approaches for measuring the level of CEA present in a specimen of sera or plasma have been described in the prior art. In one approach the plasma is pretreated with perchloric acid solvent in order to separate CEA from interferring proteineous material in the plasma. This approach employs a long time dialysis procedure (about 24 hours), followed by an immunoassay method utilizing 50% saturated ammonium sulfate or zirconyl phosphate gel.

In the second approach, no pretreatment of plasma or sera is used. Instead the plasma is subjected to a double antibody treatment [Egan, et al., Immunochem. 9 (1972) 289]. This approach suffers the disadvantage of requiring a long time period (two or three days) to complete the assay.

The third approoch [Hirai, H., Cancer Res., 37 (1977) 2267] involves a procedure which uses a paper disc solid phase radioimmunoassay technique. This approach makes use of the so-called sandwich immunoassay technique [solid support-antibody-antigen-labeled antibody: Catt, K. and Tregar, G., Science, 158 (1967) 1570]. In this technique serum or plasma is heat-treated for ten minutes at 85 degrees centigrade in an acetate buffer at pH 5.0. Thereafter, the supernatant is separated and then incubated for approximately five hours with a paper disc to which antibody against CEA (anti-CEA) has been covalently attached. Subsequently, $^{125}$I labeled anti-CEA is added and incubated for approximately 20 hours. The results from use of this approach are obtained after approximately 25 hours.

Unexpectedly it has been found that substituting solid supports having CEA antibody adsorbed thereto for paper disc having CEA antibody covalently bound thereto provides a more sensitive immunoassay. The time for the assay using CEA antibody adsorbed solid support is about one fifth that of the procedure using a paper disc.

SUMMARY OF THE INVENTION

This invention relates to a method for measuring the level of carcinoembryonic antigen (CEA) in a sample of plasma or sera and, therefore, represents a convenient method to aid in the diagnosis of cancer. The method comprises the steps of: heat-treating the test sample to precipitate interfering protein and provide a supernatant containing carcinoembryonic antigen, and separating the supernatant from the precipitated protein; incubating the supernatant with a solid support having carcinoembryonic antigen antibody adsorbed thereto, thereby binding carcinoembryonic antigen from the supernatant to said antibody; separating the supernatant from and washing the solid support to remove unbound carcinoembryonic antigen; incubating the solid support with a solution of labeled carcinoembryonic antigen antibody, thereby binding said labeled antibody to the solid support; separating the solution from and washing the solid support to remove unbound labeled carcinoembryonic antigen antibody; and measuring the labeled carcinoembryonic antigen antibody either bound to the solid support or in the solution.

DETAILED DESCRIPTION OF THE PRESENT INVENTION

Serum or plasma samples are prepared from whole blood by conventional techniques.

The serum or plasma sample is diluted with buffer and the mixture is heated to precipitate interfering protein. The precipitated proteins are separated by filtration or decantation generally after centrifugation.

Solution of weak acids and their salts buffering at pH of about 5 are suitable diluents for serum or plasma. Thus, solutions of acetic acid, succinic acid, boric acid, citric acid, trichloroacetic and salts thereof buffering at pH of about 5 are suitable. About 2–5 volumes of diluent are added to 1 volume of sample.

The diluted sample is heated at 65°–86° C. for 10–20 minutes to selectively precipitate interfering protein in the presence of CEA, a glycoprotein.

A preferred pretreatment of sample involves diluting a volume of serum or plasma with about 4 volumes of 0.2 molar acetate buffer pH about 5, mixing, heating the mixture at 70° C. for about 15 minutes, centrifuging the resulting precipitate and decanting the CEA containing supernatant.

CEA-antibody adsorbed to a solid support or metal, glass or plastic [J. Lab. and Clin. Med. 70, 820, 1967 and Science, 158, 1570, 1967] is used as a reagent in the present invention. Plastic supports having antibody adsorption properties similar to polystyrene are suitable for practicing the present invention. Polystyrene beads and tubes having CEA-antibody adsorbed thereto are preferred reagents.

Another reagent used in the present invention is labeled CEA-antibody.

Techniques for labeling antibodies wth iodine-125 ($^{125}$I) or other radioactive labels are well known: Greenwood, Hunter and Glover, Biochem. J., 89:114, (1963) and Biochem. 13, 1014, (1974).

Techniques for fluorescently labeling antibodies are also well known: Feltkamp, Immunology 18, 875 (1970) and U.S. Pat. No. 3,789,116.

Likewise, enzymes such as catalase, peroxidase β-glucuronidase, glucose-6-phosphate dyhydrogenase, urease, and glucoseoxidase are conveniently linked to antibodies by art recognized techniques: U.S. Pat. Nos. 3,875,011; 3,791,932 and 3,879,262.

The present invention combines heat treating in sample preparation with "sandwich" immunoassay techniques to provide an unexpectedly sensitive and fast assay. Thus, the previously described supernatant from heat treated sample is incubated for about 1–4 hours with a solid support having CEA antibody adsorbed. CEA in the supernatant is bound to the CEA antibody on the solid support. After washing with water or buffer to remove unbound CEA from the solid support, the solid support is incubated for 1–4 hours with labeled CEA antibody. The support is again washed to remove unbound labeled CEA antibody and labeled CEA antibody on the solid support is measured. The measured system is represented as follows:

Plastic solid support-(adsorbed CEA-antibody)-CEA-(labeled CEA antibody). The prior art system is as follows:

Paper disc solid support-(covalently linked CEA-antibody)-CEA-(labeled CEA-antibody). This difference significantly increases sensitivity of the assay and reduces assay time.

The equilibrium binding of CEA to antibody-coated solid support at 45° C. is nearly achieved after an incubation period of about 10 hours. However, 50% of the equilibrium binding of CEA is attained after only two hours at 45° C. Incorporation of two-hour incubation steps permit the CEA assay to be performed in less than five hours.

The preferred embodiment of the present invention comprises the steps of: heat-treating the test sample, buffered at about pH 5.0, at about 65°–85° C., to precipitate interfering protein and provide a supernatant containing carcinoembryonic antigen, and separating the supernatant from the precipitated protein; incubating the supernatant with a plastic solid support having carcinoembryonic antigen antibody adsorbed thereto, thereby binding carcinoembryonic antigen from the supernatant to said antibody; separating the supernatant from and washing the solid support to remove unbound carcinoembryonic antigen; incubating the solid support with radiolabeled carcinoembryonic antigen antibody, thereby binding said radiolabeled antibody to the solid support; separating the solution from and washing the solid support to remove unbound radiolabeled carcinoembryonic antigen antibody; and measuring the radiolabeled carcinoembryonic antibody bound to the solid support.

In a most preferred embodiment, the heat-treating step is performed at 70° C. for about 15 minutes and; the CEA antibody is labeled with $^{125}I$; and the incubation steps are performed over a period of 1–4 hours each.

The following examples are set out to illustrate the present invention and not to limit it in spirit or scope.

EXAMPLE I

A 0.4 ml plasma or serum sample is placed in a 13×100 cm polystyrene disposable test tube, and diluted with 1.6 ml of 0.2 molar solution of acetate buffer at pH 4.9±0.1. After mixing on a vortex mixer, the tube is covered with a piece of polyethylene film and incubated preferably at 70° C. for 15 minutes and allowed to cool to room temperature. The insoluble material is separated from the supernatant by centrifugation for ten minutes at 1700× g. The glycoprotein containing supernatant is used in the CEA assay procedure.

The standard CEA samples are prepared in 0.2 molar acetate buffer pH 4.9±0.1 containing 0.1% bovine serum albumin.

1.1 ml of buffer (0.01 M Tris-HCl, 0.15 M NaCl, pH 9) containing 300 μg/ml gamma-globulin fraction of guinea pig anti-CEA serum [obtained by techniques of Tomita, et al., Immunol., 26, 291 (1974), and Anderson, et al., Immunochem. 12, 577 (1975)] is used to coat a 13×100 mm polystyrene tube. The coating solution is incubated in the tube for about 16 hours at 37° C. and then for two hours at 4° C. After removing the coating solution, the tube is stored in 1.0 ml of 0.01 M Tris-saline solution containing 0.01% azide pH 7 at 4° C. and washed with the same solution just prior to further use.

Goat anti-CEA is radiolabeled with $^{125}I$ by the insoluble lactoperoxidase method [David, et al., Biochem. 13, 1014 (1974)].

To establish a standard curve, 1.0 ml of 0.15 M phosphate buffer, pH 6.5±0.2 containing known amounts of CEA and 1% bovine serum albumin (BSA) are added to a series of the antibody coated tubes. For the unknown sample, 1.0 ml of the clear supernatant is transferred into an antibody-coated tube and then the tube is incubated for two hours at 45° C. At the end of the incubation period, the sample is aspirated and the tube washed twice with 1.5 ml portions of 0.01 M Tris-saline buffer pH 7 containing 0.01% azide. Then 1.0 ml of phosphate buffer containing $^{125}I$ labeled antibody (approximately 50 ng, 400,000 cpm) and 1% BSA is added to the tube and the tube is incubated for a second time for two hours at 45° C. After the second incubation, the solution is removed and the tube is washed twice with the Tris-saline buffer before counting in a gamma counter. The CEA levels of the unknown sample is determined from the standard curve and corrected for dilution.

EXAMPLE II

Following the procedures set out in Example I, plastic beads are coated with antibody to CEA (guinea pig) and incubated with the samples (standards, controls, and unknowns). The CEA present in the sample is bound to the solid phase with the unbound material removed by washing the beads as before. Subsequently, antibody to CEA tagged with $^{125}I$ is incubated with the bead.

Unbound anti-CEA $^{125}I$ is removed by washing. As in Example I, the count rate is proportional to the concentration of CEA in the specimen and the concentration of CEA is determined from values obtained from the CEA standards tested concurrently with the unknowns and controls.

EXAMPLE III

Table 1 presents data from a comparative study performed between the method of this invention (utilizing a polystyrene bead, to which CEA antibody has been adsorbed) and the paper disc (to which CEA antibody has been conjugated) technique in terms of sensitivity in a four-hour assay at 45° C.

The data of Table 1 was obtained making use of the procedure in Example II, wherein plastic beads are coated with antibody to CEA for a sandwich RIA. The activity of the plastic bead coated antibody to CEA is compared to commercially obtained paper disc with antibody to CEA covalently bound (conjugated). The comparison is run in side by side separate reactions using the same CEA standard and the same $^{125}I$ labeled antibody solutions.

0.2 ml sample of supernatant containing CEA is incubated separately with the anti-CEA coated bead and with the anti-CEA conjugated paper disc for two hours at 45° C. At the end of the incubation period, each sample is removed from the solid supports which are washed twice with 4–5 ml of water. Then 0.2 ml of 0.15 M phosphate buffer solution containing $^{125}I$ labeled antibody (approximately 50 ng, 480,000 cpm) and 1% BSA is added to each of the solid supports and incubated for a second time for two hours at 45° C. After the second incubation, the solution is removed and the solid supports washed twice with Tris-saline buffer before counting in a gamma counter.

Table 1 illustrates the unexpected speed and sensitivity of methods of the present invention.

TABLE 1

Comparison of Ab-adsorbed Polystyrene Bead and Ab-conjugated Paper Disc as Solid-Phase Support of CEA Immunoassays

| Purified CEA in standard solution (ng/ml) | 0 | | 0.5 | | 3 | | 10 | | 20 | |
|---|---|---|---|---|---|---|---|---|---|---|
| Solid-phase support | Disc | Bead | Disc | Bead | Disc | Bead | Disc | Bead | Disc | Bead |
| Bound $^{125}$I labeled Antibody (counts/min) | 1040 | 777 | 1271 | 1464 | 2381 | 4732 | 6083 | 13490 | 9523 | 23100 |

(1) These data represent experiments which were performed using the same CEA standard and same $^{125}$I labeled antibody solutions.
(2) Polystyrene beads were coated with anti-CEA while the paper discs had anti-CEA covalently conjugated.
(3) The reaction times were two hours for the first step and two hours for the second step at 45° C.

What is claimed is:

1. A method for measuring the level of carcinoembryonic antigen in a test sample of plasma or sera, comprising the steps of:
   (a) heat-treating the test sample to precipitate interfering protein and provide a supernatant containing carcinoembryonic antigen, and separating the supernatnant from the precipitated protein;
   (b) incubating the supernatant with a plastic solid support having carcinoembryonic antigen antibody adsorbed thereto, thereby binding carcinoembryonic antigen from the supernatant to said antibody;
   (c) separating the supernatant from and washing the plastic solid support to remove unbound carcinoembryonic antigen;
   (d) incubating the plastic solid support with a solution of labeled carcinoembryonic antigen antibody, thereby binding said labeled antibody to the solid support;
   (e) separating the solution from and wshing the plastic solid support to remove unbound labeled carcinoembryonic antigen antibody; and
   (f) measuring the labeled carcinoembryonic antigen antibody either bound to the plastic solid support or in the solution.

2. A method of measuring the level of carcinoembryonic antigen in a test sample of plasma or sera, comprising the steps of:
   (a) heat-treating the test sample, buffered at about pH 5.0, at about 65°-85° C., to precipitate interfering protein and provide a supernatant containing carcinoembryonic antigen, and separating the supernatant from the precipitated protein;
   (b) incubating the supernatant with a plastic solid support having carcinoembryonic antigen antibody adsorbed thereto, thereby binding carcinoembryonic antigen from the supernatant to said antibody;
   (c) separating the supernatant from and washing the plastic solid support to remove unbound carcinoembryonic antigen;
   (d) incubating the plastic solid support with radiolabeled carcinoembryonic antigen antibody, thereby binding said radiolabeled antibody to the plastic solid support;
   (e) separating the solution from and washing the plastic solid support to remove unbound radiolabeled carcinoembryonic antigen antibody; and
   (f) measuring the radiolabeled carcinoembryonic antigen antibody bound to the plastic solid support.

3. A method according to claim 2 wherein the heat-treating is performed at about 70° C. for about 15 minutes.

4. A method according to claim 2 wherein the plastic solid support is in the form of a bead or tube.

5. A method according to claim 4 wherein the bead or tube is polystyrene.

6. A method according to claim 2 wherein the radiolabeled carcinoembryonic antigen antibody is labeled with iodine-125.

7. A method according to claim 2 wherein the incubating steps (b) and (d) are conducted for about one to four hours.

* * * * *